United States Patent [19]
Chang et al.

[11] Patent Number: 5,972,173
[45] Date of Patent: Oct. 26, 1999

[54] ALLYL ALCOHOL PURIFICATION

[75] Inventors: Te Chang, West Chester; George F. Rowell, Exton, both of Pa.

[73] Assignee: Arco Chemical Technology, LP, Greenville, Del.

[21] Appl. No.: 09/188,803

[22] Filed: Nov. 9, 1998

[51] Int. Cl.⁶ .............................. B01D 3/40; C07C 29/84
[52] U.S. Cl. ............................ 203/57; 203/58; 203/60; 203/62; 568/913
[58] Field of Search ................... 203/60, 62, 58, 203/57; 568/913

[56] References Cited

U.S. PATENT DOCUMENTS

| | | | |
|---|---|---|---|
| 4,601,791 | 7/1986 | Berg et al. | 203/58 |
| 5,118,392 | 6/1992 | Berg | 203/60 |
| 5,152,876 | 10/1992 | Berg et al. | 568/913 |
| 5,207,876 | 5/1993 | Berg et al. | 568/913 |
| 5,772,853 | 6/1998 | Berg | 203/57 |
| 5,795,447 | 8/1998 | Berg | 203/62 |

OTHER PUBLICATIONS

Prace Naukowe Instytutu Inzynierii Chemicznej i Urzadzen Cieplnych Politechniki Wroclawskiej, No. 21; Studia i Materialy, No. 9. pp. 45–58, 1973. (English Translation).

*Primary Examiner*—Virginia Manoharan
*Attorney, Agent, or Firm*—William C. Long

[57] ABSTRACT

Mixtures of allyl alcohol and n-propanol are separated by extractive distillation using propylene carbonate, N-methyl pyrrolidone or gamma-butyrolactone extractive distillation solvent.

4 Claims, No Drawings

ALLYL ALCOHOL PURIFICATION

FIELD OF THE INVENTION

The present invention provides a process for separating n-propanol from allyl alcohol by extractive distillation.

BACKGROUND OF THE INVENTION

Allyl alcohol is an important chemical of commerce which is produced by various methods including the lithium phosphate catalyzed isomerization of propylene oxide.

Allyl alcohol produced in this fashion usually contains a small but significant amount of n-propanol which is very difficult to separate due to the closeness of the boiling points of allyl alcohol and n-propanol. Extractive distillation procedures have been proposed for the separation of n-propanol and allyl alcohol using certain extractive distillation agents such as dimethyl sulfoxide, acetamide and ethylene glycol phenylether, adiponitrile, dimethylformamide, sulfolane and the like. See U.S. Pat. No. 4,601,791, for example.

U.S. Pat. No. 5,795,447 relates to the separation of 2-butanol from isobutanol by extractive distillation with a number of extractive distillation solvents including ethylene carbonate, methyl pyrrolidone, and butyrolactone. The patent also mentions a great number of alternative extractive distillation solvents designed to accomplish the specific separation of 2-butanol from isobutanol.

Extractive distillation is, of course, by now a well known process. The general principles of extractive distillation operation are described in a great number of publications including, specifically U.S. Pat. Nos. 5,795,447 and 5,772,853.

The selection of an appropriate extractive distillation solvent is critical for accomplishing the distillation separation of closely boiling materials. The extractive distillation agent must be capable of enhancing the relative volatility of one component with respect to the other component in order that the separation be accomplished and also the solvent must be readily separable from the component with which is becomes associated. Although there are a great number of materials which have in the past been separated by extractive distillation procedures, the art at best is an empirical one and it is not feasible to ascertain in advance which solvents would accomplish a desired separation.

SUMMARY OF THE INVENTION

In accordance with the present invention, mixtures of close boiling allyl alcohol and n-propanol are separated by extractive distillation procedures using an extractive distillation solvent selected from N-methyl pyrrolidone, propylene carbonate, and gamma-butyrolactone. Mixtures of these solvents can be used but this is not preferred. It has been found that these solvents enhance the volatility of n-propanol relative to allyl alcohol, and through the use of these extractive distillation solvents, n-propanol can be separated overhead in an extractive distillation system and a stream comprised of allyl alcohol reduced in n-propanol content and also comprised of solvent can be separated as bottoms. The bottoms stream is resolved in a solvent stripper with the purified allyl alcohol recovered overhead and the bottoms solvent recovered for recycle to the extractive distillation process.

DETAILED DESCRIPTION

Reference is made to the following Table 1 which shows the effect of the addition of the various extractive distillation solvents on the relative volatilites of n-propanol and allyl alcohol. It can be seen that the extractive distillation solvents of the present invention are exceedingly effective in enhancing the relative volatility of n-propanol as compared to allyl alcohol and thus can be effectively employed in accomplishing the separation of these close boiling components.

The present invention provides a solvent extractive distillation process to accomplish the separation of allyl alcohol and n-propanol; the effective solvents are selected from N-methyl pyrrolidone, propylene carbonate and gamma-butyrolactone. The effectiveness of n-propanol and allyl alcohol separation is due to the enhancement of the volatility of n-propanol relative to allyl alcohol by the solvent. Experimental data of relative volatilities of n-propanol with respect to allyl alcohol (1 wt % n-propanol in allyl alcohol @ 730 mm Hg) as a function of solvent concentration in the liquid are as follows:

TABLE 1

| | | | |
|---|---|---|---|
| N-Methyl Pyrrolidone in Liquid, wt % | 0 | 52.4 | 83.3 |
| Solvent/Feed Ratio | 0 | 1.1 | 5.0 |
| Ref. Volatility * | 1.02 | 1.29 | 1.41 |
| Propylene Carbonate in Liquid, wt % | 0 | 53.2 | 83.0 |
| Solvent/Feed Ratio | 0 | 1.1 | 4.9 |
| Rel. Volatility * | 1.02 | 1.20 | 1.33 |
| Gamma-butyrolactone in Liquid, wt % | 0 | 51.9 | 83.1 |
| Solvent/Feed Ratio | 0 | 1.1 | 4.9 |
| Rel. Volatility * | 1.02 | 1.24 | 1.38 |

* N-Propanol/allyl alcohol

As shown by the above data, n-propanol becomes more volatile with respect to allyl alcohol as the extractive solvent concentration is increased. An extractive distillation procedure using this discovery for accomplishing n-propanol and allyl alcohol separation is illustrated by the following:

Crude allyl alcohol containing about 1 wt % n-propanol is fed to the near bottom of an extractive distillation column while solvent is fed near the top of the column, the extractive column typically has 30–50 theoretical trays.

The extractive distillation column bottoms comprised of allyl alcohol and solvent are sent a stripper having typically 20–35 theoretical trays for allyl alcohol and solvent separation while n-Propanol reduced allyl alcohol product is recovered as overhead from the column. Solvent recovered as stripper bottoms is sent back to the extractive distillation column top. A typical solvent to allyl alcohol feed weight ratio is from 1–10 to maintain an extractive solvent concentration on the distillation trays at an effective level. A reflux to distillate weight ratio of 1–8 is appropriate and the solvent feed location should be at least several trays below the top to avoid significant solvent. The allyl alcohol feed tray should be located well below the solvent feed tray to provide sufficient extractive distillation stages to allow effective allyl alcohol and n-propanol separation. Trays in the stripping section are necessary to effectively strip residual n-propanol from allyl alcohol/solvent at the bottom of the extractive distillation column section.

For crude allyl alcohol containing lights and heavies, a heavies column may be added to the purification scheme before the extractive distillation column for heavies and aldehyde removal with caustic injection. The extractive distillation column removes n-propanol as well as other light impurities. Product allyl alcohol with purity greater than 99% and less than 0.12 wt % n-propanol may be produced economically by the suggested method. In general, allyl alcohol containing minor amounts of n-propanol, eg. less than about 8 wt %, preferably less than about 4 wt % and most preferably 1 wt % or less are resolved by the process of the invention.

The following example illustrates practice of the invention using N-methyl pyrrolidone as the extractive distillation solvent.

Impure allyl alcohol containing 0.56 wt % n-propanol is fed at the rate of 9612 lbs/hr to an extractive distillation column having 45 theoretical trays. The feed is at the 35th tray from the top. N-methyl pyrrolidone is fed to the 5th tray from the top at the rate of 48060 lbs/hr.

An overhead stream is removed at 207° F. and 15 psia at the rate of 288 lbs/hr, this stream having a composition by weight of 9.4% n-propanol, 90.6% allyl alcohol and 0.3 ppm solvent.

A bottoms stream is removed at 341° F. and 17.2 psia and is passed to a stripping column having 30 theoretical trays at the 15th tray from the top. An overhead allyl alcohol stream containing 0.28 wt % n-propanol is separated at the rate of 9315 lbs/hr at 207° F. and 15 psia. Bottoms solvent N-methyl pyrrolidone is removed at the rate of 48069 lbs/hr and at 405° F. and 16 psia and is cooled and recycled.

Results similar to the above are obtained with propylene carbonate and gamma-butyrolectone as solvents in the extractive distillation separation.

I claim:

1. A method for separating a mixture consisting essentially of n-propanol and allyl alcohol which comprises distilling said mixture in the presence of an extractive distillation solvent consisting essentially of a member selected from the group consisting of propylene carbonate, N-methyl pyrrolidone and gamma-butyrolactone and separating n-propanol overhead from a mixture of solvent and allyl alcohol reduced in n-propanol content.

2. The method of claim 1 wherein the extractive distillation solvent is propylene carbonate.

3. The method of claim 1 wherein the extractive distillation solvent is N-methyl pyrrolidone.

4. The method of claim 1 wherein the extractive distillation solvent is gamma-butyrolactone.

* * * * *